US00PP30080P2

(12) United States Plant Patent
Mukundan

(10) Patent No.: US PP30,080 P2
(45) Date of Patent: Jan. 8, 2019

(54) ***AGLAONEMA* PLANT NAMED 'MUKGEMPREM'**

(50) Latin Name: *Aglaonema hybrida*
Varietal Denomination: MUKGEMPREM

(71) Applicant: Parthasarathy Mukundan, Tamil Nadu (IN)

(72) Inventor: Parthasarathy Mukundan, Tamil Nadu (IN)

( * ) Notice: Subject to any disclaimer, the term of this patent is extended or adjusted under 35 U.S.C. 154(b) by 0 days.

(21) Appl. No.: 15/731,898

(22) Filed: Aug. 21, 2017

(51) Int. Cl.
*A01H 5/12* (2018.01)

(52) U.S. Cl.
USPC ..... Plt./376

(58) Field of Classification Search
USPC ..... Plt./376
CPC ... A01H 5/02; A01H 5/12; A01H 5/00; A01H 6/00
See application file for complete search history.

*Primary Examiner* — June Hwu
(74) *Attorney, Agent, or Firm* — C. A. Whealy

(57) ABSTRACT

A new and distinct cultivar of *Aglaonema* plant named 'MUKGEMPREM', characterized by its upright, outwardly arching and uniform plant habit; freely clumping habit; vigorous and robust growth habit; rapid growth rate; relatively short internodes giving a compact, dense and full plant form; glossy dark green-colored leaves with greyed green chevrons and undulating margins; dark green-colored leaf petioles; and relative tolerance to low temperatures.

3 Drawing Sheets

Botanical designation: *Aglaonema hybrida.*
Cultivar denomination: 'MUKGEMPREM'.

BACKGROUND OF THE INVENTION

The present invention relates to a new and distinct cultivar of *Aglaonema* plant, botanically known as *Aglaonema hybrida* and hereinafter referred to by the name 'MUKGEMPREM'.

The new *Aglaonema* plant is the product of a controlled breeding program conducted by the Inventor in Tiruporur, Chennai, India. The objective of the breeding program is to create new compact and dense *Aglaonema* plants with good plant vigor, interesting and unique leaf shapes and variegation patterns, resistance to pathogens and pests and tolerance to low temperatures.

The new *Aglaonema* plant is a naturally-occurring branch mutation of *Aglaonema hybrida* 'Gemini', not patented. The new *Aglaonema* plant was discovered and selected by the Inventor on Jul. 10, 2011 on a single plant from within a population of plants of 'Gemini' in a controlled nursery environment in Tiruporur, Chennai, India.

Asexual reproduction of the new *Aglaonema* plant by cuttings and divisions in a controlled environment in Tiruporur, Chennai, India since August, 2011 has shown that the unique features of this new *Aglaonema* plant are stable and reproduced true to type in successive generations of asexual reproduction.

SUMMARY OF THE INVENTION

Plants of the new *Aglaonema* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MUKGEMPREM'. These characteristics in combination distinguish 'MUKGEMPREM' as a new and distinct *Aglaonema* plant:

1. Upright, outwardly arching and uniform plant habit.
2. Freely clumping habit.
3. Vigorous and robust growth habit.
4. Rapid growth rate.
5. Relatively short internodes giving a compact, dense and full plant form.
6. Glossy dark green-colored leaves with greyed green chevrons and undulating margins.
7. Dark green-colored leaf petioles.
8. Relatively tolerant to low temperatures.

Plants of the new *Aglaonema* differ primarily from plants of the mutation parent, 'Gemini', in the following characteristics:

1. Plants of the new *Aglaonema* are more uniform in plant form and shape than plants of 'Gemini'.
2. Plants of the new *Aglaonema* are more robust, denser and bushier than plants of 'Gemini'.
3. Leaves of plants of the new *Aglaonema* are not deformed whereas leaves of plants of 'Gemini' commonly exhibit leaf apex distortion.

Plants of the new *Aglaonema* can be compared to plants of *Aglaonema hybrida* 'Mary Ann', disclosed in U.S. Plant Pat. No. 8,976. In side-by-side comparisons plants of the new *Aglaonema* differ primarily from plants of 'Mary Ann' in the following characteristics:

1. Plants of the new *Aglaonema* are more uniform in plant form and shape than plants of 'Mary Ann'.
2. Leaves of plants of the new *Aglaonema* are longer and broader than leaves of plants of 'Mary Ann'.
3. Plants of the new *Aglaonema* and 'Mary Ann' differ in leaf coloration as leaves of plants of 'Mary Ann' are duller and paler green in color than leaves of the new *Aglaonema.*

4. Plants of the new *Aglaonema* are more low temperature tolerant than plants of 'Mary Ann'.

Plants of the new *Aglaonema* can also be compared to plants of *Aglaonema hybrida* 'Maria', not patented. In side-by-side comparisons plants of the new *Aglaonema* differ primarily from plants of 'Maria' in the following characteristics:

1. Plants of the new *Aglaonema* are more uniform in plant form and shape than plants of 'Maria'.
2. Plants of the new *Aglaonema* are faster-growing than plants of 'Maria'.
3. Plants of the new *Aglaonema* are more freely clumping and denser and fuller than plants of 'Maria'.
4. Leaves of plants of the new *Aglaonema* are longer and broader than leaves of plants of 'Maria'.
5. Plants of the new *Aglaonema* and 'Maria' differ in leaf coloration as leaves of plants of 'Maria' are duller and lighter green in color than leaves of the new *Aglaonema*.
6. Plants of the new *Aglaonema* are more low temperature tolerant than plants of 'Maria'.

BRIEF DESCRIPTION OF THE PHOTOGRAPHS

The accompanying photographs illustrate the overall appearance of the new *Aglaonema* plant showing the colors as true as it is reasonably possible to obtain in colored reproductions of this type. Colors in the photographs may differ slightly from the color values cited in the detailed botanical description which accurately describe the colors of the new *Aglaonema* plant.

The photograph on the first sheet is a side perspective view of a typical plant of 'MUKGEMPREM' grown in a container.

The photograph on the second sheet is side comparison view of typical plants of 'MUKGEMPREM' (left) and 'Mary Ann' (right) grown in containers.

The photograph on the third sheet is close-up comparison view of typical plants of 'MUKGEMPREM' (left) and 'Maria' (right).

DETAILED BOTANICAL DESCRIPTION

The aforementioned photographs and following observations and measurements describe plants grown in 15.25-cm containers in Miami, Fla. during the spring and early summer in a polypropylene-covered shadehouse. Plants were grown under environmental conditions and cultural practices which approximate those generally used in commercial *Aglaonema* production. During the production of the plants, day temperatures ranged from 25° C. to 32° C. and night temperatures ranged from 15° C. to 23° C. Plants were one year old when the photographs and the detailed description were taken. In the following description, color references are made to The Royal Horticultural Society Colour Chart, 2007 Edition, except where general terms of ordinary dictionary significance are used.

Botanical classification: *Aglaonema hybrida* 'MUKGEMPREM'.

Parentage: Naturally-occurring branch mutation of *Aglaonema hybrida* 'Gemini', not patented.

Propagation:

*Type*.—By top cuttings, stem cuttings and divisions.

*Time to initiate roots, summer*.—About 21 to 28 days at temperatures about 25° C. to 32° C.

*Time to initiate roots, winter*.—About 30 to 40 days at temperatures about 12° C. to 25° C.

*Time to produce a rooted young plant, summer*.—About 30 to 35 days at temperatures about 25° C. to 32° C.

*Time to produce a rooted young plant roots, winter*.—About 45 to 60 days at temperatures about 12° C. to 25° C.

*Root description*.—Medium in thickness, fleshy; typically off-white in color, actual color of the roots dependent on substrate composition, water quality, fertilizer, substrate temperature and age of roots.

*Rooting habit*.—Freely branching; profuse, dense.

Plant description:

*Plant and growth habit*.—Upright and somewhat outwardly arching plant habit; freely clumping habit; relatively short internodes giving a compact, dense, full and symmetrical habit; vigorous and robust growth habit; developing leaves initially upright, then arching outwardly with development.

*Plant height, from soil level to top of leaf plane*.—About 51 cm.

*Plant diameter or spread*.—About 47 cm.

*Stem description*.—Clumping habit: Plants of the new *Aglaonema* are freely clumping with about six clumps developing per container. Aspect: Mostly upright. Strength: Strong; somewhat flexible. Diameter, at the base: About 1.9 cm. Internode length, at the base: About 1.2 cm. Color: Darker than 147A.

Leaf description:

*Arrangement*.—Alternate to whorled; simple.

*Length*.—About 26 cm.

*Width*.—About 8.5 cm.

*Shape*.—Elliptic.

*Apex*.—Acuminate with short aristate tip; to date, no distortion of leaf apices have been observed on plants of the new *Aglaonema*.

*Base*.—Obtuse.

*Margin*.—Entire; moderately undulate.

*Texture and luster, upper surface*.—Smooth, glabrous; glossy.

*Texture and luster, lower surface*.—Smooth, glabrous; moderately glossy.

*Venation pattern*.—Pinnate.

*Color*.—Developing leaves, upper surface: Ground color, darker and more green than 146A; chevrons, close to more green than 146B. Developing leaves, lower surface: Close to 146A to 146B. Fully expanded leaves, upper surface: Ground color, darker green than 147A; chevrons, close to 189A; venation, similar to lamina colors. Fully expanded leaves, lower surface: Lighter green than 147A; mid-vein, close to 147B; lateral venation, close to 147A.

*Petioles*.—Aspect: Mostly erect, outwardly arching with development. Length: About 15 cm. Diameter, distal: About 5.5 mm by 6 mm. Diameter, proximal, flattened: About 4.5 cm. Strength: Strong; flexible. Color, distal: Close to 147A. Color, proximal: Close to 147A. Wing length: About 10 cm. Wing diameter, base: About 6 mm. Wing color, inner and outer surfaces: Close to 147A.

Inflorescence description:

*Inflorescence arrangement*.—Hooded spathes surrounding a columnar spadix borne on a arching scape; spadix with sessile, simple female and male flowers separated into two zones; female flowers develop at the base of the spadix; male flowers develop on distally on the spadix.

*Fragrance*.—Faint, sweet and pleasant.

*Spathe*.—Length: About 8 cm. Width: About 1.5 cm. Shape: Elliptic. Apex: Acuminate. Base: Attenuate. Margin: Entire. Texture and luster, front and rear surfaces: Smooth, glabrous; glossy. Color, front surface: Close to 145D. Color, rear surface: Close to 145A.

*Spadix*.—Length, overall: About 4.5 cm. Length, male flower zone: About 4 cm. Length, female flower zone: About 5 mm. Diameter, male flower zone: About 6 mm. Diameter, female flower zone: About 6.5 mm. Shape: Columnar, spindle-shaped. Apex: Obtuse. Aspect: Upright. Color, mature, male zone: Close to 158A to 158B. Color, mature, female zone: Close to 150C. Male flowers: Quantity per spadix: Numerous. Shape: Dumbbell-shaped. Size: About 1.5 mm by 1 mm. Pollen amount: None observed. Female flowers: Quantity per spadix: About 12 to 20. Shape: Ovoid. Height: About 2 mm. Diameter: About 2.5 mm. Stigma color: Close to 150D. Ovary color: Close to 144B.

*Scape*.—Length: About 9 cm. Diameter: About 4 mm. Strength: Sturdy; flexible. Aspect: Outwardly arching. Texture and luster: Smooth, glabrous; matte. Color: Close to 146A.

*Seeds and fruits*.—Seed and fruit development have not been observed on plants of the new *Aglaonema* to date.

Disease & pest resistance: Plants of the new *Aglaonema* have not been observed to be resistant to pathogens or pests common to *Aglaonema* to date.

Temperature tolerance: Plants of the new *Aglaonema* have been observed to be relatively low temperature tolerant and to tolerate temperatures ranging from about 10° C. to about 38° C.

It is claimed:

1. A new and distinct *Aglaonema* plant named 'MUK-GEMPREM' as illustrated and described.

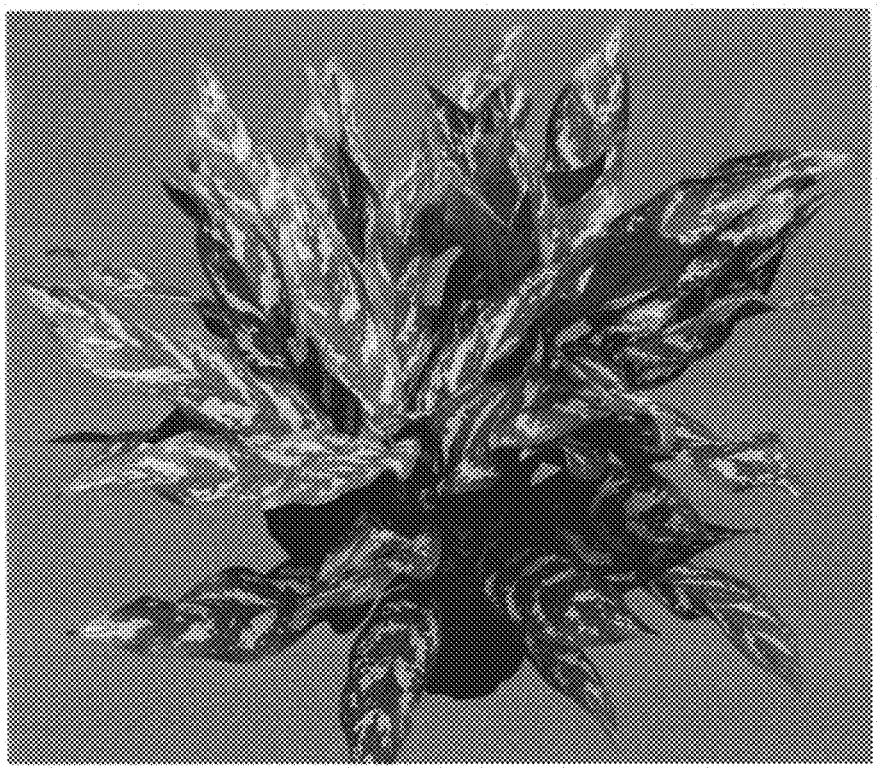

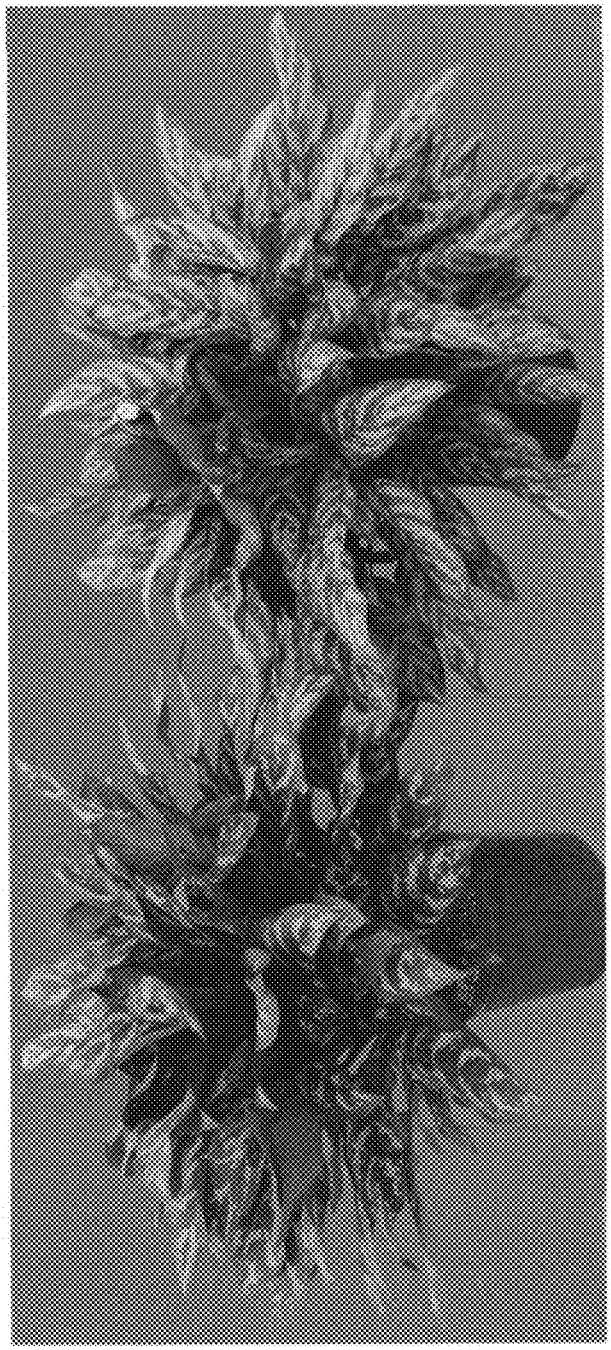

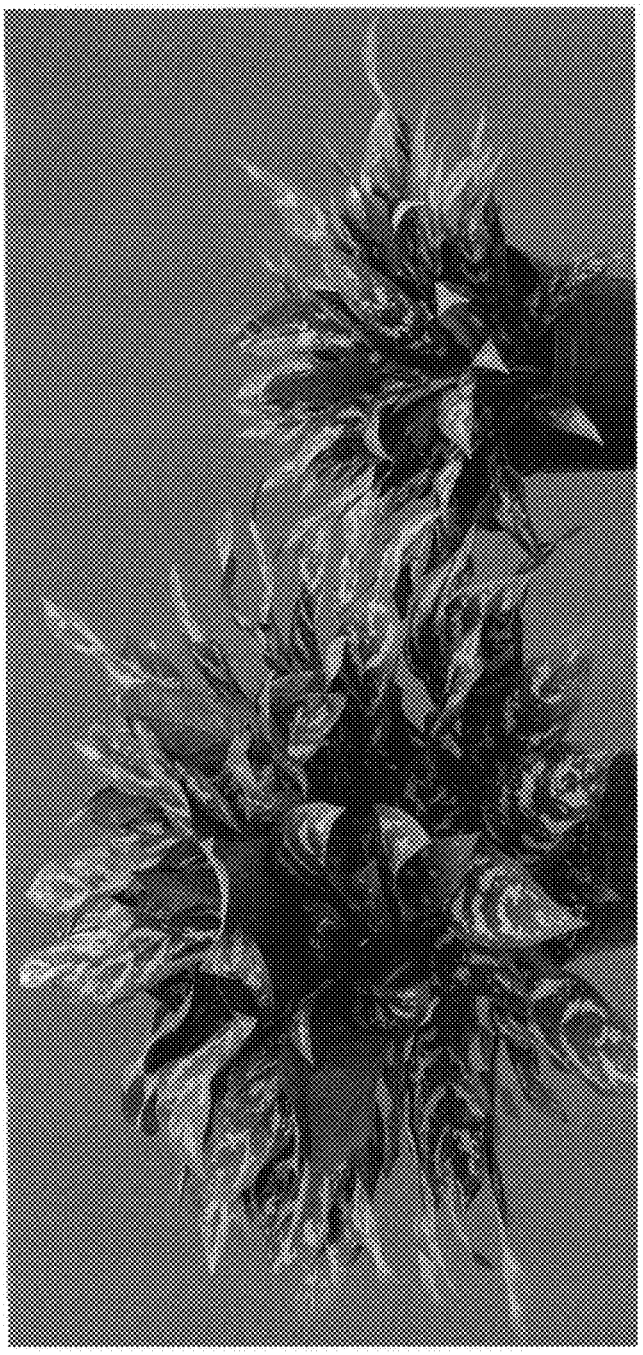

* * * * *